United States Patent [19]
Urick et al.

[11] Patent Number: 5,666,969
[45] Date of Patent: Sep. 16, 1997

US005666969A

[54] GUIDEWIRE HAVING MULTIPLE RADIOSCOPIC COILS

[75] Inventors: Michael J. Urick, Rogers; Thomas J. Bachinski, Lakeville; Richard R. Prather, Rogers; Marian L. Larson, Buffalo, all of Minn.

[73] Assignee: SciMed Life Systems, Inc., Maple Grove, Minn.

[21] Appl. No.: 425,933

[22] Filed: Apr. 20, 1995

Related U.S. Application Data

[63] Continuation-in-part of Ser. No. 245,726, May 18, 1994, Pat. No. 5,497,783.

[51] Int. Cl.⁶ ................................................ A61B 5/00
[52] U.S. Cl. ................................. 128/772; 128/657
[58] Field of Search ................................. 128/657, 772; 604/164, 170, 280, 282

[56] References Cited

U.S. PATENT DOCUMENTS

| | | | |
|---|---|---|---|
| 4,964,409 | 10/1990 | Tremulis | 128/772 X |
| 5,209,730 | 5/1993 | Sullivan | 604/96 |

*Primary Examiner*—Sam Rimell
*Attorney, Agent, or Firm*—Nawrocki, Rooney & Sivertson

[57] ABSTRACT

An intraluminal guidewire for use in medical procedures in general, and cardiovascular procedures in particular. A core wire is formed as the inner member of the guidewire. A distal helical coil is fixedly attached to the distal end of the core wire. A proximal helical coil is fixedly attached to the core wire proximally of the distal coil. The proximal end of the distal coil and the distal end of the proximal coil can be fixedly mounted in spaced relation on a flexible spacer sleeve. The two coils can be of different materials, such as stainless steel and gold, having significantly differing degrees of radiopacity. The sleeve can be a third degree of radiopacity, preferably selected to show a dark spot on a fluoroscope. The coils can be attached to the core wire by a flexible adhesive.

23 Claims, 8 Drawing Sheets

GUIDEWIRE HAVING MULTIPLE RADIOSCOPIC COILS

RELATED APPLICATION

This is a continuation-in-part of U.S. patent application Ser. No. 08/245,726, filed May 18, 1994, now U.S. Pat. No. 5,497,783 for GUIDEWIRE HAVING RADIOSCOPIC TIP, by Urick et al. The entire disclosure of application Ser. No. 08/245,726 is incorporated by reference herein.

BACKGROUND OF THE INVENTION

The present invention relates in general to intraluminal medical devices, and more particularly to guidewires or core wires for intraluminal devices including catheters, and means for proper location of such intraluminal devices within the body.

The use of intraluminal catheters for treatment of various medical problems within the body is well known. It is also well known that a variety of difficulties may be encountered as the catheter is steered through the selected lumen to a desired point within the body. The path may be tortuous and the point of interest may be difficult to locate precisely. To overcome these difficulties, a flexible guidewire may first be inserted into the vascular lumen to the desired location. Once a guidewire is in position, a desired catheter may then be slid over the guidewire to reach the desired situs in the body.

It can readily be seen that it is important to have a guidewire that is flexible enough to traverse the tortuous vascular system. It can also be readily seen that it is important to have a guidewire that is radioscopic such that the physician can verify the position or location of the guidewire within the vascular lumen.

A continuing series of technical improvements and additions have been made in the catheter field to provide devices and methods which can overcome certain of these difficulties. One such series of improvements has resulted in the now well known use of a thin flexible guidewire having a tapered distal section that can be more easily steered through the lumen by forces applied to a proximal section. Because the distal section of a tapered guidewire may lose pushability, another improvement that has been developed is the use of a coiled wire helix which is wrapped around the distal tapered section of the guidewire. The coiled wire helix may improve the pushability of the distal tapered section of the guidewire while maintaining overall flexibility.

An example of a guidewire having a coiled wire helix is disclosed in U.S. Pat. No. 4,619,274 issued to Morrison. Morrison discloses a core member having a proximal and a distal end wherein the core member has a decreasing cross sectional area in a direction toward the distal end. The decreasing cross sectional area is incremental in that the core member comprises a plurality of fixed diameter cylinders which are coupled together by tapered sections. The diameters of the fixed diameter cylinders become smaller in the direction of the distal end of the core member.

Morrison further discloses a tapered coil which is carried and secured to the core element and extends over the core element. The tapered coil has a proximal end and a distal end wherein the diameter of the tapered coil decreases toward the distal end. Furthermore, the coil is formed of wire having a diameter which decreases toward the distal end. The improvements suggested by Morrison may provide some increased pushability while maintaining a degree of flexibility. However, the decreasing diameter core member and tapered coil may limit the pushability of the distal tip of the core member.

Another example of a guidewire having a coiled wire helix is disclosed in U.S. Pat. No. 4,846,186 issued to Box et al. In Box et al., a core member having an initial uniform diameter segment tapers along a uniform portion to a second constant diameter segment. A flexible spring tip surrounds, and is attached to, the second constant diameter segment and extends distally therefrom. The core member again tapers in a region where the flexible spring separates from the core member. Within the flexible spring, a portion of the core member is flattened to increase the flexibility of the distal portion of the core member. The flattened core and spring are brazed together at an extreme distal tip portion to form a distal guidewire tip.

A further variant of a guidewire having a reduced diameter distal portion surrounded by a coil wire helix is disclosed in U.S. Pat. No. 4,538,622 to Samson et al. The guidewire disclosed in Samson et al. includes an elongated stainless steel core wire having a reduced diameter distal portion including two constant diameter portions and two tapered portions.

The reduced diameter distal portion is surrounded by a first proximately disposed coil and a second distally disposed coil. The proximate coil is preferably stainless steel and is soldered at its proximal end to the core wire. The distal coil is preferably formed from a radiopaque material such as gold or platinum to allow location of the distal end of the guidewire by fluoroscopy. Under a fluoroscope, the radiopaque coil will appear brightly.

The proximal end of the distal end coil is threaded into the distal end of the proximal coil. The coils are joined into a unitary assembly by brazing. The brazing also secures the coils to the core wire. The brazing however, fills the space between the coils and the wire over a length of the reduced diameter portion. This consequently increases the effective diameter of the core wire abruptly, thus changing the core wire's flexibility at the braze or solder.

SUMMARY OF THE INVENTION

The present invention pertains to a guidewire providing an alternate means for fluoroscopic location without introducing abrupt and substantial changes in the guidewire's flexibility. A preferred embodiment of a guidewire in accordance with the present invention includes a core wire having proximal and distal sections, the distal section preferably comprising various segments wherein each segment has a reduced or tapered diameter. A distal helical coil of a first material having a first degree of radiopacity is used to encase or cover the tip end of the distal section in the manner well known in the art and described in the above-defined, related application and the described prior art. A second or proximal helical coil is also provided to surround a portion of the core wire proximal to the distal coil, which proximal coil is of a second material having a second degree of radiopacity.

In one embodiment, the distal and proximal coils are spaced by a flexible sleeve member which preferably is made of a heat shrinkable material such as PTFE (polytetrafluoroethylene), FEP (fluorinated ethylene propylene) or POC (polyolefin copolymer). The sleeve preferably surrounds the core wire at a point between the two helical coils and has a degree of radiopacity which causes it to appear as a dark spot on a fluoroscope. This visible spacing between two coils of differing radiopacity significantly enhances the operators ability to position the guide wire within the body. The dark spot can be correlated to the bright marker found on most prior art intraluminal catheters to indicate the relative position between the guide wire and the catheter during placement in the body.

The presence of the elastic or flexible sleeve between the adjacent coils will enhance the steerability and relative flexibility of the guidewire compared to having the coils directly attached to one another. The coils are connected to the core wire by a flexible adhesive to reduce abrupt changes in the guidewire's flexibility caused by soldered or brazed connection of the coils to the core wire.

DETAILED DESCRIPTION OF THE PREFERRED EMBODIMENTS

Figure 1:
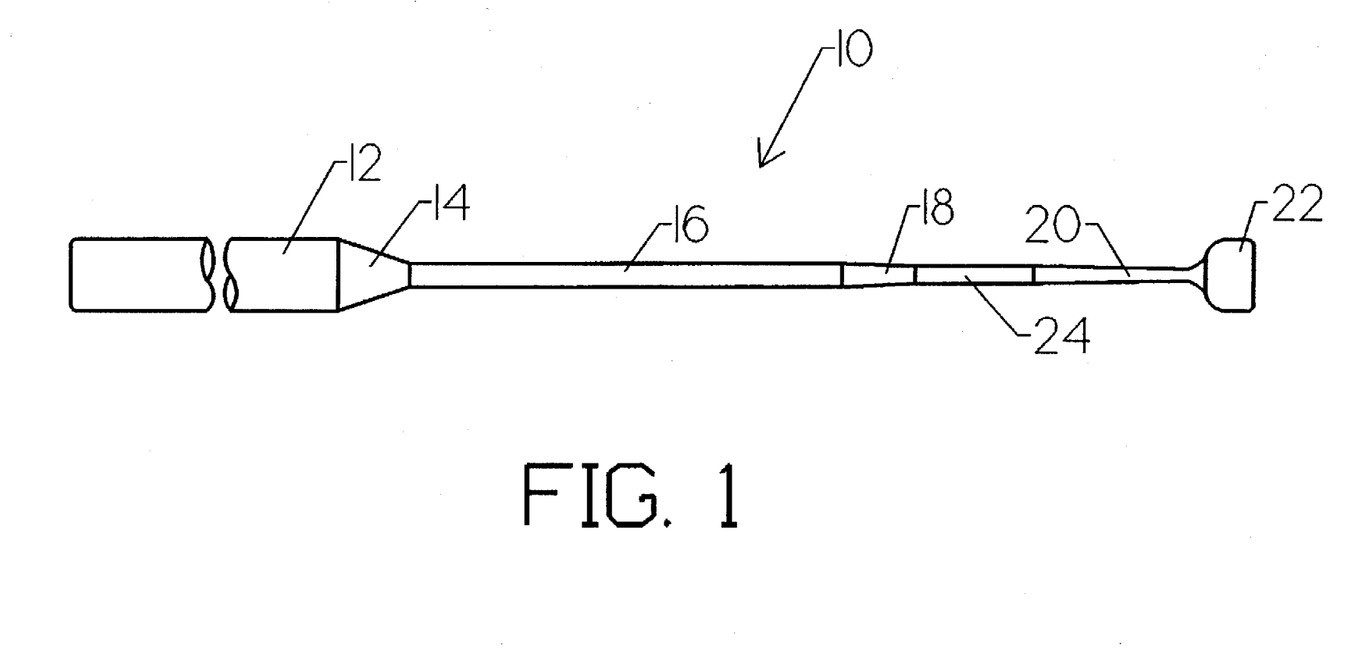
FIG. 1 is a side view of a core wire in accordance with of the present invention.

Referring now to the drawings wherein like reference numerals indicate like elements throughout the several views, and in particular to FIG. 1 which shows a first embodiment of a core wire 10 in accordance with the present invention. The guidewire of the preferred embodiments of the present invention includes a core wire, such as core wire 10 and helical coils and a sleeve (see FIG. 2 and associated text) attached at the distal end of the core wire.

Core wire 10 is preferably formed of a length (i.e. about 182 centimeters) of #304 stainless steel wire. Proximal portion 12 is about 150 centimeters and has a constant diameter of about 0.010 inch to 0.018 inch. Portion 12 may be completely coated with a lubricous coating such as PTFE (polytetrafluoroethylene) to lessen friction between the lumen wall of a catheter and the guidewire. A distal portion of core wire 10 includes a tapered portion 14, an isodiametric portion 16, a second tapered portion 18, a second isodiametric portion 24, and a tapered portion 20. The distal portion is formed by centerless grinding of the stainless steel wire. A distal portion of portion 20 may be flattened into a ribbon shape. Isodiametric portion 16 has a diameter of about 0.006 inch. A distal tip 22 has a diameter of about that of proximal portion 12. Tip 22 is used for terminating the distal portion of the helix (not shown in this view).

It can be appreciated, as well known in the art, that materials other than stainless steel may be used to form a core wire. Furthermore, these dimensions of the core wire are exemplary only, it being understood that reducing the diameter of core wire 10 increases its flexibility whereas increasing the diameter of core wire 10 decreases its flexibility.

Figure 2:
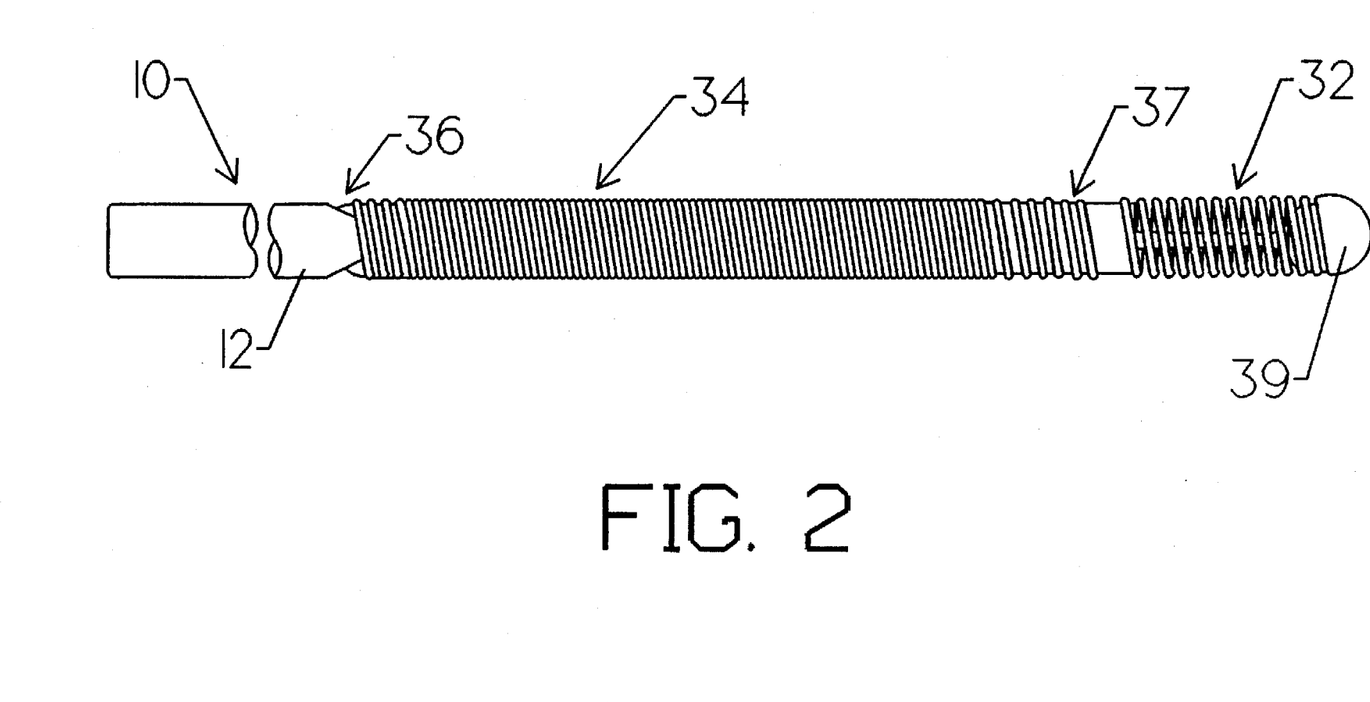
FIG. 2 is a side view of a guidewire in accordance with the present invention employing the first and second helical coils spaced by a flexible sleeve.

FIG. 2 is a side view of an assembled guidewire of this invention employing core wire 10 (see also FIG. 1) and distal and proximal helical coils 32 and 34, respectively. A ball tip 39 is formed by soldering or brazing or otherwise attaching distal helix 32 and distal tip 22 of core wire 10, thus permanently joining them. Proximal section 36 of proximal coil 34 is similarly soldered or brazed or otherwise attached to section 14 of core wire 10. Alternately, either or both of these connections can be made by a flexible adhesive.

To complete the embodiment of FIG. 2, the distal end of helix 34, and the proximal end of helix 32 are shown attached to core wire 10. The attachment is preferably made by flexible adhesive. Coils 32 and 34 preferably have differing radiopacity by, for example, forming coil 32 from platinum and coil 34 from stainless steel. Preferably a sleeve 37 disposed between coils 32 and 34 has low radiopacity such that a space is left between the two helical coils, such that a dark spot will appear between the coils 32 and 34 during fluoroscopy. Coils 32 and 34 can be coated with silicone.

The resultant improvement in the ease and accuracy of location of the guidewire in accordance with the present invention within a body lumen will be recognized by those of skill in the art. For example, the position of the dark spot can be correlated with the position of the bright spot on most intraluminal catheters that will be positioned by the guidewire of the present invention, such bright spots being well known and widely used by those skilled in the art. The correlation allowing the operator to determine the relative position of the guidewire and the catheter.

Figure 3:
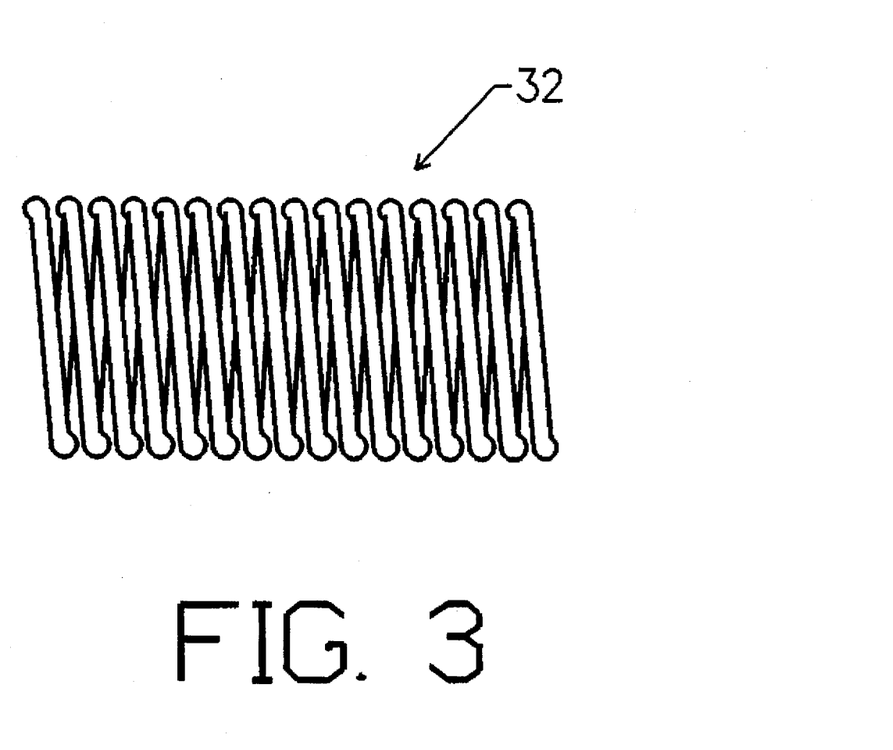
FIG. 3 is a view of a first or distal helical coil in accordance with the present invention.

FIG. 3 is a plan view of a first helical coil or distal helix 32 intended to be attached to core wire 10. Preferably, distal helix 32 is a single coil of 14 k gold wire having a circular cross section. Other similarly radiopaque materials such as platinum may be used to form coil 32. The wire has a diameter of about 0.0025 inch and the completed helix has an outside diameter approximately equal to the diameter of proximal portion 12. The coils of helix 32 may be adjacent or in spaced relation. Increased spacing between the coils generally results in a coil 32 having increased transverse flexibility.

Figure 4:
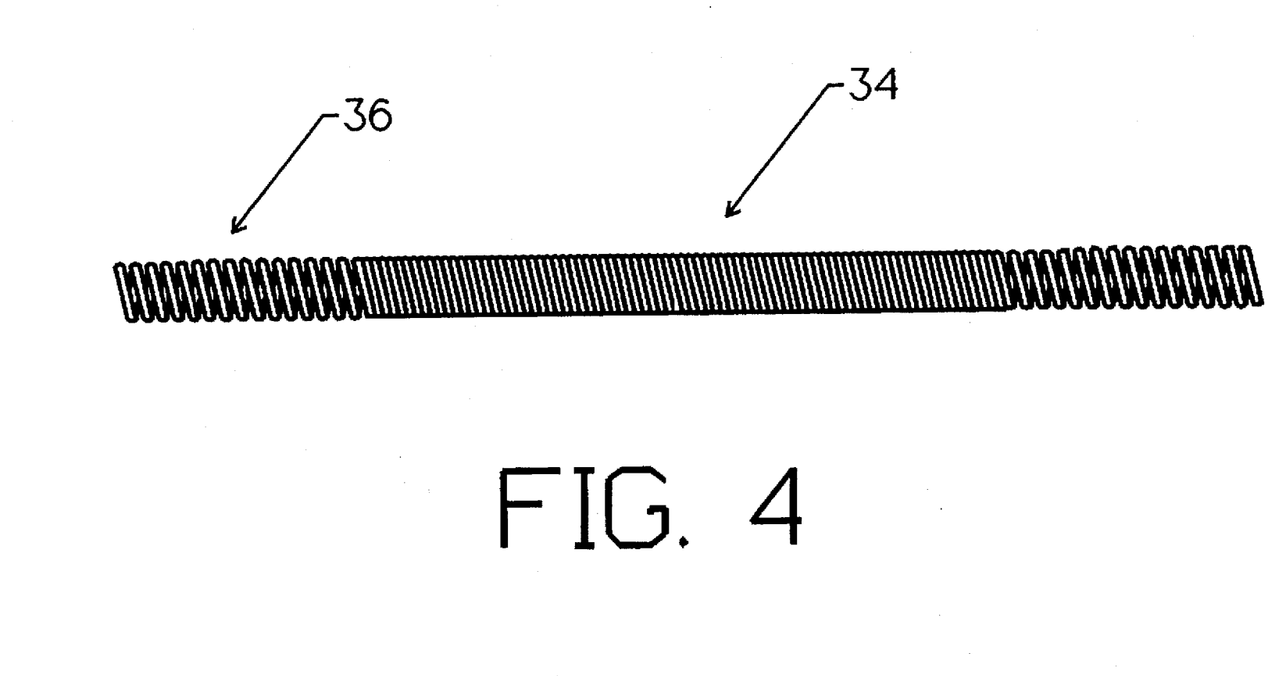
FIG. 4 is a view of a second or proximal helical coil in accordance with the present invention.

FIG. 4 is a plan view of a second helical coil or proximal helix 34. Coil 34 can, for most of its length, have a closed winding. A proximal end 36 of coil 34 is preferably a spaced winding coil for sufficient length to provide for attachment of end 36 to core wire 10. Coil 34 is preferably made of #304 stainless steel of a circular cross section. It is preferable that the material used for coil 34 have a significantly different degree of radiopacity than does coil 32; such as the difference between platinum and stainless steel as suggested above. The platinum coil can create a bright image under fluoroscopy whereas the stainless steel coil creates a ghost image.

It can be appreciated that coils 32 and 34 may be formed from wires having different diameters and flexibility characteristics as well known in the art. For example, a smaller diameter wire made from the same material as a larger diameter wire would be relatively more flexible than the larger diameter wire.

Figure 5:
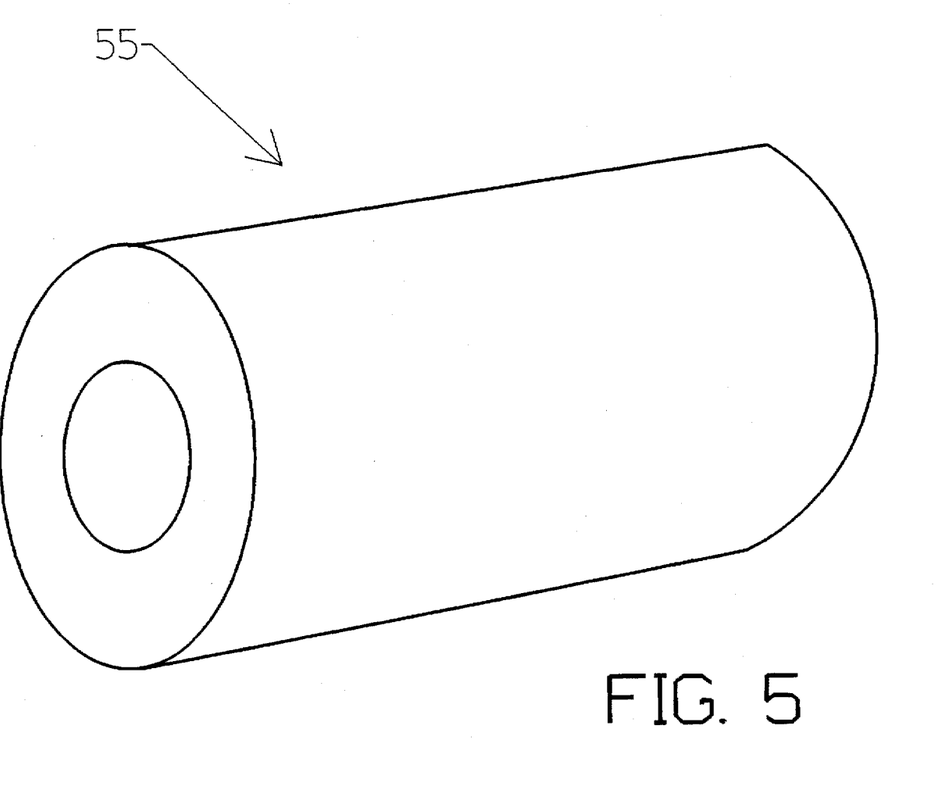
FIG. 5 is a view of the flexible spacer sleeve in accordance with the present invention.

FIG. 5 shows a view of a sleeve 37. Sleeve 37 is intended to fit around core wire 10 between coils 32 and 34. Sleeve 37 can be made of a heat shrinkable, flexible material, such as PTFE (polytetrafluoroethylene), FEP (fluorinated ethylene propylene) or POC (polyolefin copolymer).

Figure 6:
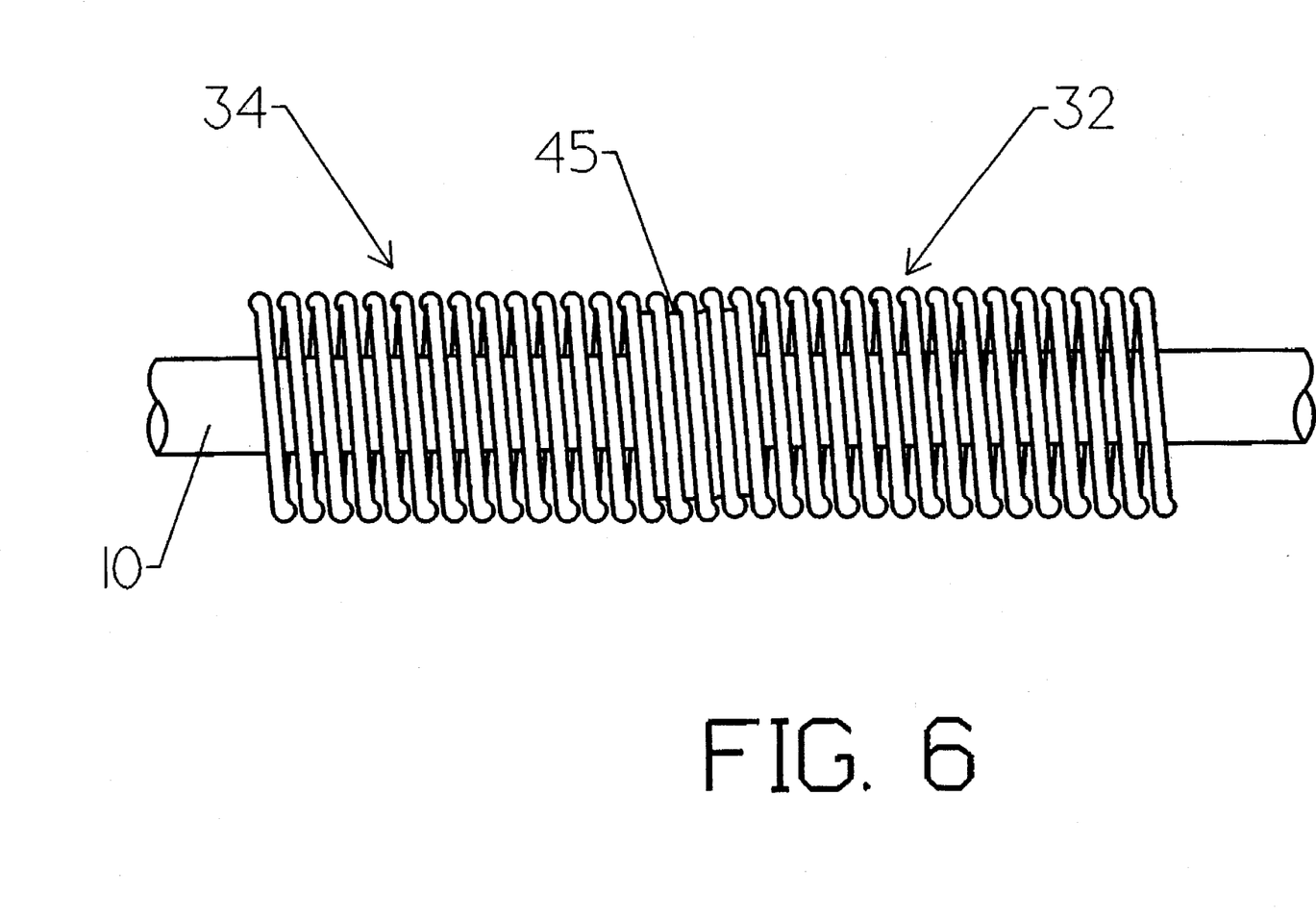
FIG. 6 is a view of a pair of helical coils connected in an alternate manner in accordance with the present invention.

FIG. 6 is a view of another embodiment of the present invention showing a pair of helical coils 32 and 34 mounted around a portion of core wire 10. Coils 32 and 34 are shown attached to core wire 10 simply by an elastic adhesive 45 without the use of a sleeve such as sleeve 37.

Figure 7A:
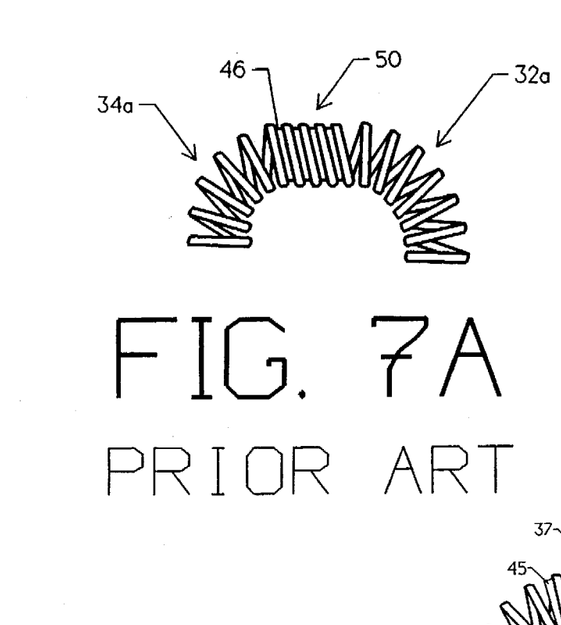
FIGS. 7a, 7b and 7c are views indicating the relative flexibility of the guidewire of the present invention over the prior art.
Figure 7B:
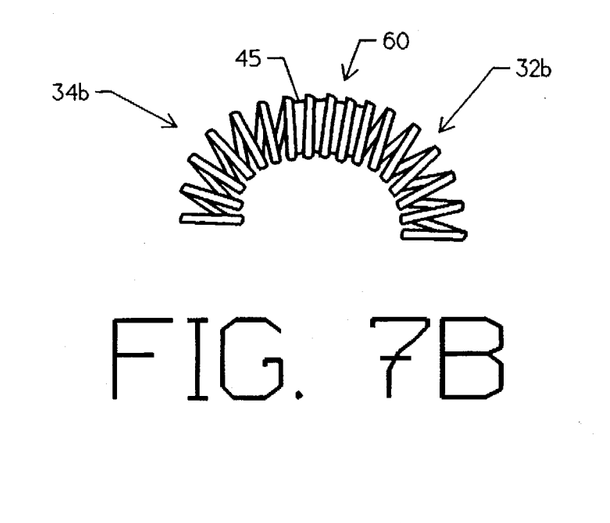
Figure 7C:
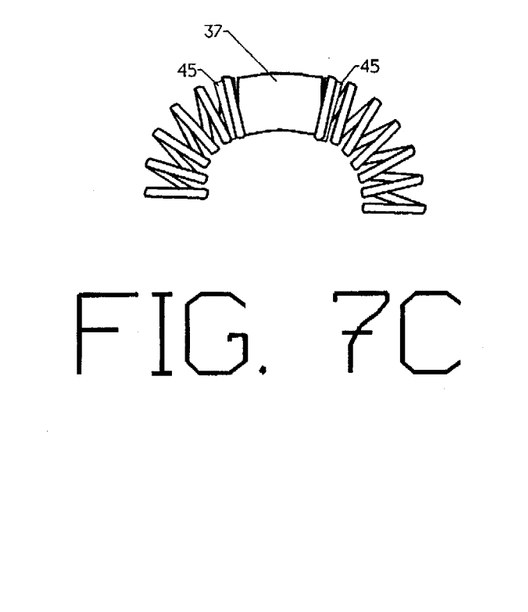

FIGS. 7a, 7b and 7c are schematic representations of the pair of coils 32 and 34 of FIG. 6 showing the difference between the attachment means of this invention and that of the prior art.

FIG. 7a depicts a pair of coils 32a and 34a which have been interconnected by a prior art medium 46. Prior art medium 46 could be solder or any other non-flexible form of attachment. As can be seen, when the attached coils 32a and 34a are bent, as would be necessary to pass the coils on a core wire through the tortuous path of a body lumen, the stiff connection 46 causes a "flat" section 50 along the surface of connected coils 32a and 34a. This undesirable deformation of the bend is caused because the stiff connection 46 prevents the free bending of a plurality of adjacent turns on each of helical coils 32a and 34a. It is apparent that this flat spot 50 may interfere with the desired trackability of a guidewire through a lumen because the flat spot can cause the guidewire to prolapse when entering a side branch vessel.

FIG. 7b depicts a pair of helical coils 32b and 34b which are attached at one end by flexible adhesive 45. As can be seen when coils 32b and 34b are bent, the adjacent coils affixed by adhesive 45 are allowed to flex relative to one another and the result is a bent area 60 that is highly preferable to the flat area 50 of FIG. 7a. Coils 32b and 34b are preferably independently connected to the core wire (not shown) by adhesive 45. Thus it can be seen that the improved attachment medium 45 of this invention provides a guidewire with a greater degree of flexibility and thus steerability for movement through a body lumen. Attachment medium 45 is preferably UV adhesive such as epoxy or acrylite.

As shown in FIG. 7c, performance similar to that shown in FIG. 7b may also be obtained when sleeve 37 is used in conjunction with flexible adhesive 45, so long as sleeve 37 is formed from sufficiently flexible material.

Figure 8:
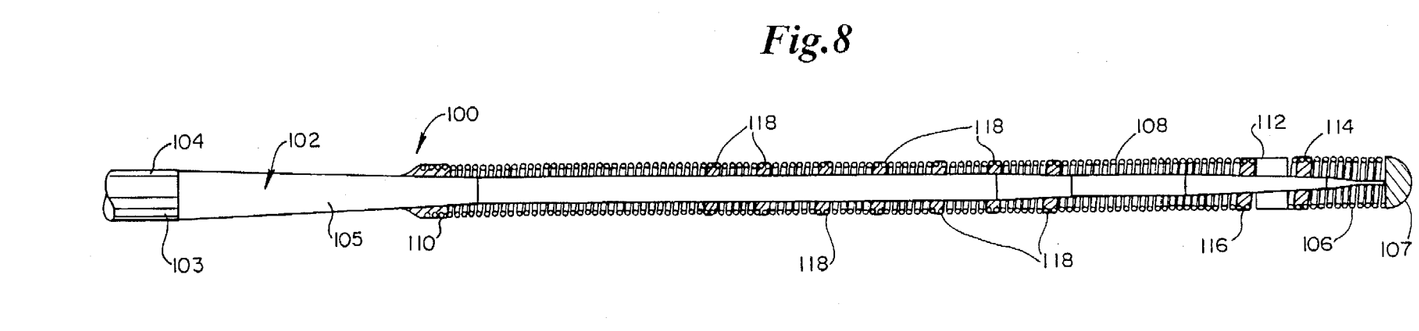
FIG. 8 is a view of an alternate embodiment of the guidewire in accordance with the present invention.

FIG. 8 is a view of an alternate embodiment of a guidewire 100 in accordance with the present invention. Guidewire 100 includes a core wire 102. Core wire 102 can be the same as core wire 10 described above. Core wire 102 includes a proximal isodiametric portion 103 which can be coated with a lubricous coating such as PTFE to lessen friction between the lumen wall of a catheter and guidewire 100. Core wire 102 also includes a distal section 105 including a plurality of tapered sections and isodiametric portions.

A distal coil 106 having a proximal end and a distal end is connected at its distal end to the extreme distal end of core wire 102. A ball tip 107 is formed by soldering, brazing, welding or the like to form the connection between the distal end of distal coil 106 and core wire 102. Distal coil 106 may be formed from the same materials as distal coil 32 described above. Like any of the coils disclosed herein, coil 106 can be covered with a silicone or hydrophilic coating.

Guidewire 100 also includes a proximal coil 108. Proximal coil 108 extends around a portion of the distal portion 105 of core wire 102 proximal of distal coil 106. Proximal coil 108 includes a proximal end and a distal end, the proximal end being fixably attached to the proximal most tapered section of distal section 105. The proximal end of proximal coil 108 can be attached to core wire 102 by a medium 110 which can be solder, braze or any adhesive such as a UV adhesive. Proximal coil 108 is preferably formed from stainless steel, but may be formed from any suitably durable biocompatible material.

A sleeve 112 is preferably disposed around core wire 102 between distal coil 106 and proximal coil 108. Sleeve 112 can be formed from the same materials as sleeve 37 described above and can be used in the same way as sleeve 37.

The proximal end of distal coil 106 and the distal end of proximal coil 108 are fixably attached to core wire 102 by bonding mediums 114 and 116, respectively. Bonding medium 114 and 116 can be solder, braze or an adhesive such as a UV adhesive.

A plurality of radiopaque solder bands 118 can be disposed around distal portion 105 of core wire 102 along a length of proximal coil 108. The solder forming bands 118 is preferably silver/tin or gold/tin solder. Although other substantially radiopaque, biocompatible solders can be used.

The spacing of marker bands 118 can be calibrated to correspond to a length measurement along core wire 102. If the spacing of bands 118 is calibrated to measure length, bands 118 can be used to make intraluminal measurements under fluoroscopy. Bands 118 can also be located across a lesion by locating the lesion by angiography and placing the portion of guidewire 100, including bands 118 across that location. If bands 118 are held in place across the lesion, intravascular devices such as angioplasty balloons and stents may be readily advanced along guidewire 100 and located across the lesion by reference to bands 118.

Figure 9:
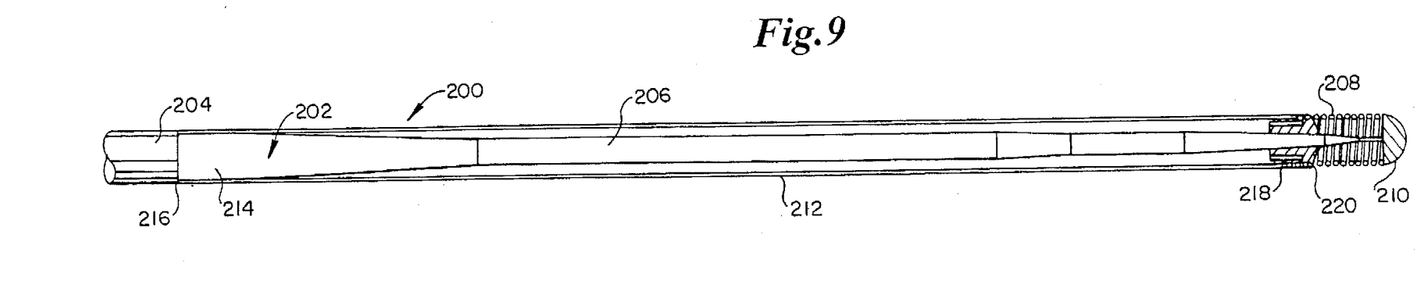
FIG. 9 is a view of another alternate embodiment of a guidewire in accordance with the present invention.

FIG. 9 shows a guidewire 200 including a core wire 202. Core wire 202 can be the same as core wire 10 described above or may be modified as described below. Core wire 202 includes a proximal portion 204 and a distal portion 206. Distal portion 206 can include several tapered portions and isodiametric portions. Proximal portion 204 and distal portion 206 can be the same as the proximal and distal portions of core wire 10 as described above. Distal portion 206, however, can be modified as described below.

Guidewire 200 preferably includes a coil 208 disposed around an extreme distal portion of core wire 202. Coil 208 can be the same as distal coils 32 and 106 described above. The distal end of coil 208 is fixedly attached to the extreme distal end of core wire 102 in the same manner as coils 32 and 106 are attached to core wires 10 and 102, respectively, to form a ball tip 210.

A metallic sleeve 212 is preferably disposed around a portion of core wire distal portion 206 proximally of coil 208. Sleeve 212 is preferably formed from a nitinol hypotube. In addition to nitinol, other highly resilient metals may be used to form sleeve 212. Metallic sleeve 212 must be flexible enough to allow guidewire 200 to be steerable through a tortuous vascular lumen, and resilient enough to avoid permanent kinking. Sleeve 212 can be coated with PTFE, silicone or a hydrophilic coating.

Proximal core wire portion 204 and sleeve 212 preferably have the same outside diameters. To provide a smooth transition between proximal portion 204 and sleeve 212, while maintaining the constant outside diameter, the proximal most tapered portion 214 can have a reduced diameter at transition 216, relative to proximal portion 204. The reduction in diameter is preferably two times the wall thickness of metallic sleeve 212.

A bridge tube 218 is preferably disposed around a portion of core wire 202 at the proximal end of coil 208 and the distal end of metallic sleeve 212. Placement of bridge tube 218 in this location is intended to urge coil 208 and sleeve 212 into coaxial alignment around core wire 202. The proximal end of coil 208 and the distal end of sleeve 212 are preferably fixedly connected to bridge tube 218 and core wire 202 by bonding medium 220 which can be a solder, braze or an adhesive such as a UV adhesive.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. An intraluminal guidewire comprising:
    an elongate core wire having a longitudinal axis, a proximal end and a distal end;
    a distal helical coil having a proximal end and a distal end and having a first degree of radiopacity, the distal end of the distal coil being fixedly attached to the distal end of the core wire;
    a proximal helical coil having a proximal end and a distal end and having a second degree of radiopacity different from the first degree of radiopacity, the proximal end of the proximal coil being fixedly attached to the core wire toward the distal end of the core wire, and the distal end of the proximal coil being proximally spaced from the proximal end of distal coil defining a longitudinal gap between the proximal and distal coils;
    a flexible polymer sleeve placed around the core wire, in the gap, longitudinally between the proximal end of the distal coil and the distal end of the proximal coil; and
    the sleeve having a third degree of radiopacity less than the first and second degrees of radiopacity.

2. A guidewire according to claim 1, wherein the third degree of radiopacity is such as to appear as a substantially dark spot when viewed through a fluoroscope.

3. A guidewire according to claim 2, wherein the spacer sleeve is made from POC.

4. A guidewire according to claim 2, wherein the proximal coil is made from stainless steel and the distal coil is made from gold or platinum.

5. A guidewire according to claim 1, further comprising a plurality of solder bands connected to the core wire along he proximal coil.

6. A guidewire according to claim 5, wherein the solder includes silver and tin.

7. A guidewire according to claim 5, wherein the solder includes gold and tin.

8. In an intraluminal guidewire having an elongate core wire having a longitudinal axis, and a plurality of spaced helical coil means of differing radiopacity serially mounted thereon, the improvement comprising:
    spacer means for spacing the coils is mounted longitudinally between adjacent helical coils, the spacer means comprises a flexible sleeve mounted around the core wire and the adjacent helical coils are mounted to the core wire.

9. The improvement of claim 8, wherein the spacer means comprises a material having a radiopacity differing from the radiopacity of each of the adjacent helical coils.

10. The improvement of claim 9, wherein the material comprises POC.

11. The improvement of claim 8, further comprising a flexible adhesive to attach the coils to the core wire.

12. The improvement of claim 8 in which said flexible adhesive includes a UV curable adhesive.

13. A guidewire according to claim 8, further comprising a plurality of solder bands connected to the core wire along the proximal coil.

14. A guidewire in accordance with claim 13, wherein the solder includes silver and tin.

15. A guidewire according to claim 13, wherein the solder includes gold and tin.

16. In a catheter guidewire including an elongate core wire having a longitudinal axis, proximal and distal ends and a plurality of spaced helical coils mounted in serial relation around said core wire and adapted to be serially connected between said core wire distal end and a point proximal of said distal end, the improvement comprising:
    flexible connection means for connecting said coils to said core wire; and
    flexible spacer means for spacing the coils mounted longitudinally between adjacent coils.

17. The improvement of claim 16 in which said flexible connection means comprises a flexible adhesive.

18. The improvement of claim 17 which said flexible adhesive includes a UV curable adhesive.

19. An intraluminal guidewire comprising:
    an elongate core wire having a proximal end and a distal end, and a reduced diameter portion proximate the distal end;
    a distal coil having a proximal end and a distal end, the distal end of the coil being fixedly attached to the distal end of the core wire and the proximal end of the coil being fixedly attached to the core wire; and
    a proximal metallic tube having a proximal end and a distal end, the metallic sleeve surrounding at least a portion of the reduced diameter portion of the core wire proximal of, and proximate the coil.

20. An intraluminal guidewire in accordance with claim 19, further comprising a bridge tube, the bridge tube being disposed around the core wire at the distal end of the tube and the proximal end of the coil.

21. An intraluminal guidewire in accordance with claim 20, wherein the distal end of the tube is fixedly attached to the core wire at the bridge tube.

22. An intraluminal guidewire in accordance with claim 21, wherein the distal end of the tube and the proximal end of the coil are fixedly attached to the core wire at the bridge tube by a UV adhesive.

23. An intraluminal guidewire in accordance with claim 21, wherein the distal end of the tube and the proximal end of the coil are fixedly attached to the core wire at the bridge tube by soldering.

* * * * *